(12) United States Patent
Yin et al.

(10) Patent No.: US 9,833,171 B2
(45) Date of Patent: Dec. 5, 2017

(54) MONITORING OF VITAL BODY SIGNALS DURING MOVEMENT

(75) Inventors: Bin Yin, Eindhoven (NL); Steven Antonie Willem Fokkenrood, 's-Hertogenbosch (NL); Haris Duric, Helmond (NL); Teun Van Den Heuvel, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 769 days.

(21) Appl. No.: 13/813,436

(22) PCT Filed: Jul. 27, 2011

(86) PCT No.: PCT/IB2011/053338
§ 371 (c)(1),
(2), (4) Date: Jan. 31, 2013

(87) PCT Pub. No.: WO2012/017355
PCT Pub. Date: Feb. 9, 2012

(65) Prior Publication Data
US 2013/0131525 A1 May 23, 2013

(30) Foreign Application Priority Data
Aug. 4, 2010 (EP) .................................. 10171865

(51) Int. Cl.
*A61B 5/113* (2006.01)
*A61B 5/11* (2006.01)
(Continued)

(52) U.S. Cl.
CPC ............ *A61B 5/11* (2013.01); *A61B 5/02055* (2013.01); *A61B 5/02444* (2013.01);
(Continued)

(58) Field of Classification Search
CPC ............ A61B 5/02055; A61B 5/02438; A61B 5/02444; A61B 5/0816; A61B 5/11;
(Continued)

(56) References Cited

U.S. PATENT DOCUMENTS

| | | | | |
|---|---|---|---|---|
| 5,134,369 A | * | 7/1992 | Lo | .......................... G01V 3/081 324/202 |
| 6,049,730 A | * | 4/2000 | Kristbjarnarson | . A61B 5/04011 600/509 |

(Continued)

FOREIGN PATENT DOCUMENTS

| | | |
|---|---|---|
| WO | 2006123691 | 11/2006 |
| WO | 2008018810 A2 | 2/2008 |

(Continued)

OTHER PUBLICATIONS

Hung et al, Estimation of Respiratory Waveform using an Accelerometer, 2008, 5th IEEE International Symposium on Biomedical Imaging, pp. 1493-1496.*

(Continued)

*Primary Examiner* — Jacqueline Cheng
*Assistant Examiner* — Angeline Premraj (57) ABSTRACT

In a multi-sensor system and method of monitoring vital body signals during movement of a body of a human or an animal, acceleration sensors are placed at body locations in such a way that an acceleration angle change induced by the vital body signals differs between the at least two acceleration sensors. The retrieval of the vital body signals is achieved by extracting a wanted vital body signal based on measurement results from multiple sensors that may be motion contaminated. Three retrieval schemes are proposed, each with preferred sensor locations that provide optimal performance of retrieving the vital body signal(s).

12 Claims, 4 Drawing Sheets

(51) Int. Cl.
*A61B 5/0205* (2006.01)
*A61B 5/00* (2006.01)
*A61B 5/024* (2006.01)
*A61B 5/08* (2006.01)

(52) U.S. Cl.
CPC .......... *A61B 5/1135* (2013.01); *A61B 5/7214* (2013.01); *A61B 5/02438* (2013.01); *A61B 5/0816* (2013.01); *A61B 5/6823* (2013.01)

(58) Field of Classification Search
CPC ... A61B 5/1135; A61B 5/6823; A61B 5/7214; A61L 35/11
See application file for complete search history.

(56) References Cited

U.S. PATENT DOCUMENTS

| | | | |
|---|---|---|---|
| 6,997,882 | B1 | 2/2006 | Parker et al. |
| 2004/0059210 | A1 | 3/2004 | Stetson |
| 2005/0052444 | A1* | 3/2005 | Shirai .................. G06T 11/206 345/204 |
| 2005/0240086 | A1 | 10/2005 | Akay |
| 2006/0122525 | A1 | 6/2006 | Shusterman |
| 2007/0032748 | A1* | 2/2007 | McNeil ................ A61B 5/1038 600/595 |
| 2008/0076567 | A1* | 3/2008 | Dohta .................... A63F 13/10 463/37 |
| 2008/0221398 | A1* | 9/2008 | Ronchi ................ A61B 5/0488 600/301 |
| 2008/0243021 | A1 | 10/2008 | Causevic et al. |
| 2009/0131809 | A1* | 5/2009 | Huang ................ A61B 5/0816 600/529 |
| 2010/0145171 | A1 | 6/2010 | Park et al. |
| 2012/0302900 | A1 | 11/2012 | Yin et al. |

FOREIGN PATENT DOCUMENTS

| | | |
|---|---|---|
| WO | 2009031064 A2 | 3/2009 |
| WO | 2009138896 A1 | 11/2009 |

OTHER PUBLICATIONS

Phan et al, Estimation of respiratory waveform and heart rate using an accelerometer, 2008, Conf Proc IEEE Eng Med Biol Soc., pp. 4916-4919.*

Lay-Ekuakille, Advances in Biomedical Sensing, Measurements, Instrumentation and Systems: vol. 55 of Lecture Notes in Electrical Engineering, 2009, Springer Science & Business Media, pp. 135-137.*

Rutgers University, Changes in Thoracic Volume that Lead to the Flow of Air During Inspiration and Expiration, 2003, Web, Retrieved from: http://www.bio.rutgers.edu/~gb102/lab_10/10i3r.html.*

Kudd, The Sternal Angle in Man, 1903, The Journal of Anatomy and Physiology Normal and Pathological, Human and Comparative, 37: lxvi-lxxvi.*

Bouten, C. V. C., et al.; A Triaxial Accelerometer and Portable Data Processing Unit for the Assessment of Daily Physical Activity; 1997; IEEE Trans. on Biomedical Engineering; 44(3)136-147.

Jin, A., et al.; Performance Evaluation of a Tri-axial Accelerometry-based Respiration Monitoring for Ambient Assisted Living; 2009; IEEE 31st Intl. Conf. of EMBS; pp. 5677-5680.

Karvounis, E. C., et al.; Fetal heart rate detection in multivariate abdominal ECG recordings using non-linear analysis; 2008; IEEE 30th Intl. Conf. of EMBS; pp. 2141-2144.

Reinvuo, T., et al.; Measurement of Respiratory Rate with High-Resolution Accelerometer and EMFit Pressure Sensor; 2006; IEEE Sensors Applications Symposium; pp. 192-195.

* cited by examiner

MONITORING OF VITAL BODY SIGNALS DURING MOVEMENT

FIELD OF THE INVENTION

The present invention relates to a multi-sensor system and method of monitoring a vital body sign or signal of a body of a human or an animal.

BACKGROUND OF THE INVENTION

Vital body signs or signals are measures of physiological statistics, often taken by health professionals, in order to assess the most basic body functions. The act of taking vital signs normally entails recording body temperature, pulse rate (or heart rate), blood pressure, and respiratory rate, but may also include other measurements. Vital body signs or signals, such as heart rate and respiration rate, are important indicators of a person's health status. In hospitals, patients' vital body signs or signals are monitored, either continuously in intensive care units (ICUs), or in a spot-check fashion in wards, to prevent unnoticed deterioration of a patient's condition.

There are also needs for monitoring vital body signs or signals at a home environment. As a result of ageing of the population, more elderly people live alone at home who mostly suffer from chronic diseases and thus need monitoring of their body conditions that can be reflected by the change in vital body signs or signals. The same need holds for patients who are just discharged from hospitals and still require monitoring to avoid re-hospitalization.

In lifestyle applications, measurement of vital body signs or signals is also desired, for example, during physical exercises in a fitness center to help energy expenditure assessment and more generally body condition analysis. This applies in professional sport as well.

In measuring vital body signs or signals, motion artifact is a well known issue, which refers to the degradation of measurement quality caused by activities of measured subjects. Activities affecting measurement include posture change, movement, talking, coughing and etc. The severity of this issue increases from hospital settings where patients are most of time bed tied, through home healthcare that is basically a free-living environment, and to monitoring fitness exercises where subjects are intensively moving.

One way to deal with motion artifact is to pick up 'good' parts of the measured vital body signal that are not contaminated and discard the 'bad'. Typically, when a measured subject is sleeping or at rest without much movement, a vital body sign or signal of a good quality can be obtained. This approach works in hospitals where patients are most of time bed tied and under supervision, thus with good availability of meaningful data, and it is therefore affordable to discard motion artifact contaminated data that usually results from the patient moving around and thus very probably not at risk anyway.

However, cancelling or dropping data leads to information loss, especially when patients' vital body signs or signals during activities are interesting for diagnostic purposes. Furthermore, in home healthcare, subjects are often much more mobile with their everyday activities, and the motion artifact rejection approach may result in inadequate frequency of measurement. In lifestyle applications, such as doing fitness and playing in other sports, there is also a need of monitoring vital body signs or signals continuously while the subject is active, for the purpose of energy expenditure estimation or physical condition assessment. Therefore, a new approach is asked for that, instead of discarding data of a low quality, is able to reliably retrieve vital body signs or signals from these data.

SUMMARY OF THE INVENTION

It is an object of the present invention to provide an improved method and system for monitoring vital body signs or signals of a body of a human or an animal.

This object is achieved by a method as claimed in claim 1 and by a multi-sensor system as claimed in claim 8.

Accordingly, an improved monitoring approach is proposed where monitoring vital body signs or signals during movement is enabled by extracting the vital body signs or signals from motion artifacts using a multi-sensor system with acceleration sensors adapted to measure an acceleration vector. The arrangement of the proposed system is low cost, unobtrusive, power saving and suitable for a prolonged period of monitoring on free-living subjects without imposing restrictions on their daily activities.

According to a first aspect, the retrieving may comprise estimating based on the measurement results of an orientation of said acceleration sensors, calculating a rotation matrix of the at least two acceleration sensors, aligning coordinate systems of the at least two acceleration sensors by virtually rotating the at least two acceleration sensors, and cancelling motion components not induced by the vital body signals. Thereby, motion induced components can be removed to retrieve a desired vital body sign or signal.

According to a second aspect which can be combined with the above first aspect, the retrieving may comprise transforming possibly correlated variables of the measurement results into a smaller number of uncorrelated variables, extracting parameters or features from the uncorrelated variables, and deciding on the vital body signals based on the extracted parameters or features. Hence, principal component analysis (PCA) is not used to compress data, but to extract the vital body signals from the sensors' PCA signal.

According to a third aspect which can be combined with any one of the above first and second aspects, the retrieving may comprise selecting one of the at least two acceleration sensors as reference sensor, virtually rotating the others of the at least two acceleration sensors towards the reference sensor to remove motion components, and applying the PCA to obtain the vital body signals. By cascading common mode cancellation with PCA, an improved retrieval quality can be achieved.

According to a fourth aspect which can be combined with any one of the above first and third aspects, the retrieving may comprise measuring an angle difference between acceleration vectors of the at least two acceleration sensors. This differential angle measurement approach is intrinsically robust against motion-induced interference.

According to an exemplary implementation of the fourth aspect, the placing may comprise aligning the at least two acceleration sensors in such a way that their measurement axes are substantially in the same spatial plane. Thereby, particularly breathing motion results in desired changes in the relative orientations of the acceleration sensors.

According to a fifth aspect which can be combined with any one of the above first and fourth aspects, the at least two acceleration sensors may be advantageously used in respiration sensing as inclinometers to reflect abdomen or chest movement caused by respiration or in pulse sensing to catch mechanical vibration caused by heart pumping.

According to a sixth aspect which can be combined with any one of the above first and fifth aspects, the signal extracting unit may comprise a computing unit that runs an algorithm to perform the extraction of the vital body signals. This enables implementation as a computer program product comprising code means for producing the retrieving step when run on the computing unit or device.

In exemplary implementations, the two acceleration sensors may be bi-axial or tri-axial accelerometers.

These and other aspects of the invention will be apparent from and elucidated with reference to the embodiments described hereinafter.

DETAILED DESCRIPTION OF EMBODIMENTS

In the following embodiments, a monitoring approach is proposed where monitoring vital body signs or signals during movement is enabled by using a multi-sensor system with acceleration sensors configured to measure an acceleration vector.

The proposed monitoring system comprises at least two sensors that are placed at certain locations of a human body (or animal body) that are relevant to the measured vital sign signals (i.e. vital body signs or signals). In an exemplary software-based implementation, a computing unit may run an algorithm that makes use of readouts of multiple sensors to extract a wanted vital body signal, for instance, respiration, from contaminated measurement due to motion artifacts. When multiple vital body signals are to be extracted, for instance, both respiration and heartbeat, parallel algorithms may be run serving for respective purposes. The computing unit may also run algorithms that calculate parameters from the extracted vital body signals, such as respiration rate, heart rate and their variations, and store them either locally at a storage medium or at a remote central station via a wireless link for further analysis. Of course, the monitoring system may be implemented with a hard-wired signal extracting device, unit or signal processor adapted to perform a signal processing according to the above algorithms, as explained later in more detail.

Since respiration, heart rates, and their variability are usually the most interesting vital body sign parameters, acquisition of these signals may be achieved by tri-axial accelerometers, while the use of other types of sensor is not excluded. As described for example in T. Reinvuo et al, "Measurement of respiratory rate with high-resolution accelerometer and EMFit Pressure Sensor", in IEEE Sensors AppL Symposium, February 2006, pp. 192-195, a tri-axial accelerometer is a device that measures the acceleration in three sensing axes, and is used in respiration sensing as an inclinometer to reflect the abdomen or chest movement caused by respiration, and in pulse (indirect measurement of heart beating) sensing to catch mechanical vibration at the skin caused by heart pumping. When it is required to measure both signals with a single tri-axial accelerometer, the accelerometer may be placed on the left costal arch, roughly one-third way to the sternum.

In the following embodiments, a number of measurement scenarios is proposed where, depending on which vital signal is measured and which processing method is used, sensors will be placed at body locations that are preferred for that scenario.

As already mentioned, retrieval of the vital body signal(s) can be done by a computing unit that runs an algorithm or by a signal extracting unit to extract a wanted vital body signal based on measurement results from multiple sensors that may be motion contaminated. Three retrieval schemes are proposed in different embodiments, each with preferred sensor locations that provide optimal performance of retrieving the vital body signal(s).

A first embodiment is directed to common mode cancellation (CMC) processing, wherein at least two acceleration sensors are employed, preferably tri-axial accelerometers. They are attached to different locations at a subject's torso, at which locations a targeted vital body sign signal gets optimally measured when the subject is at rest. During movement, when the sensors are properly co-located, motion-induced components will appear as 'common mode' in the sensors' acceleration vector signals, whereas the vital body signal is measured differently by individual sensors. Making use of this fact, the vital body signal may be retrieved in the presence of motion artifacts.

Figure 1:
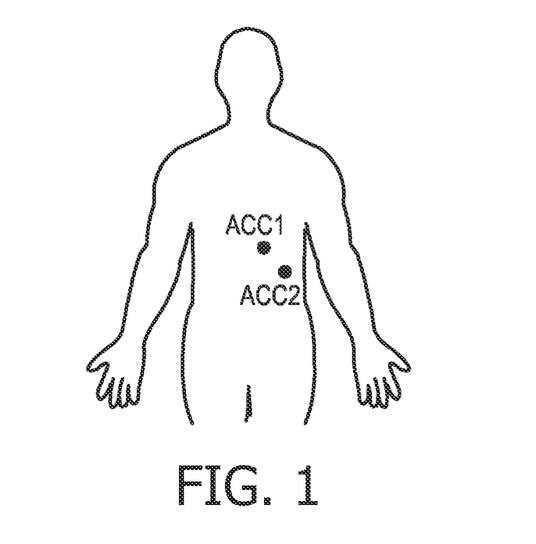
FIG. 1 shows examples of sensor locations in respiration measurement.

A respiration measurement using tri-axial accelerometers is now described as an example of the first embodiment and as depicted in FIG. 1. In this example, two tri-axial accelerometers ACC1 and ACC2 are placed on the left chest of the measured subject. In general, the sensors ACC1 and ACC2 may be placed anywhere in the chest-abdomen region that is proper for respiration sensing, i.e. that an angle change induced by the desired vital body signal(s) differs between the two sensors ACC1 and ACC2. In this example, their locations are chosen in such a way that the angle change of the multiple sensors induced by respiration differs as much as possible from one another. The example is based on a biosensor application, wherein sensor locations are selected for respiration measurement.

The readout vectors of the two sensors ACC1 and ACC2 can be expressed as:

$$V_{acc}^{(1)} = V_{resp}^{(1)} + V_{mot}^{(1)}, \quad (1)$$

$$V_{acc}^{(2)} = V_{resp}^{(2)} + V_{mot}^{(2)}, \quad (2)$$

where $V_{acc}^{(i)}$, $V_{resp}^{(i)}$, and $V_{mot}^{(i)}$ (i=1, 2) represent the measured acceleration vector signal and its respiration and motion induced components, respectively, from the i-th sensor. With a tri-axial accelerometer, the signal is a vector in the sensor coordinate system defined by readouts from x, y and z axes. It should be noticed that for respiration sensing what is (mainly) measured is the change of the gravity projected onto sensor axes caused by breathing movement. Thus, an accelerometer is used here as an inclinometer. Any inertial acceleration, normally generated at a higher frequency band, is assumingly filtered out in signal pre-processing.

Because a human torso is relatively rigid, the sensors ACC1 and ACC2 experience the same rotational change during movement, especially when they are placed close to each other so that relative movement among sensors, for instance due to skin stretch, is minimized. After the sensors ACC1 and ACC2 are aligned, that is, rotate one towards the other until they get parallel for each of their three axes, their gravitational vector components become equal.

On the other hand, respiration movement is basically volume expansion and compression of the torso. The sensors ACC1 and ACC2 are located at different points of the torso and therefore experience, due to its curved surface, different rotational movement. Consequently, the respiration induced signal components differ, even with the sensors ACC1 and ACC2 being aligned with each other.

Figure 2:
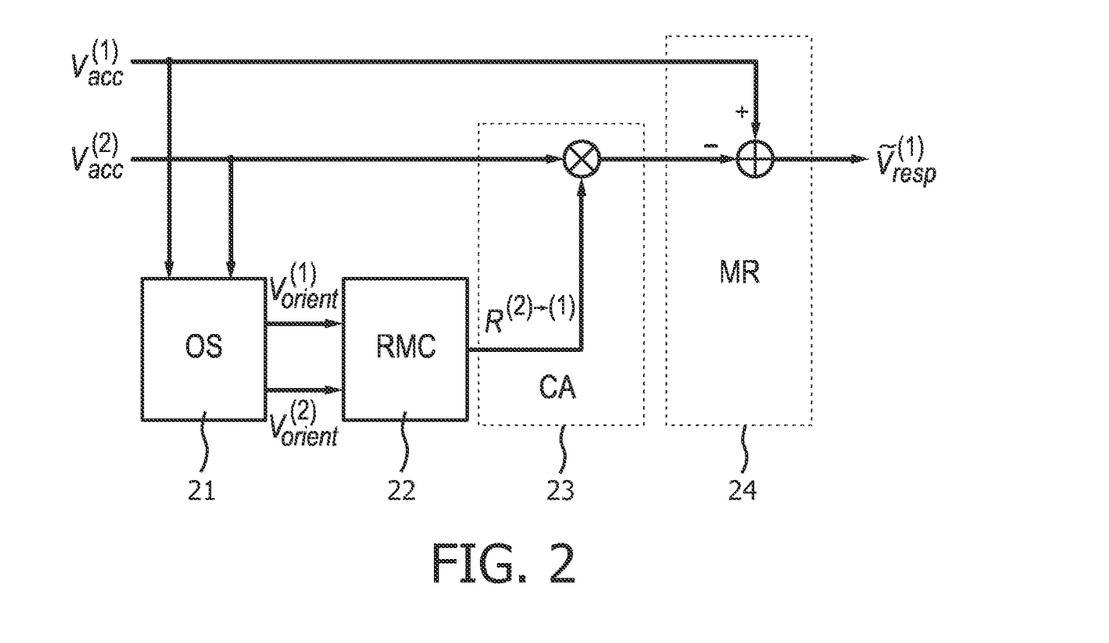
FIG. 2 shows a schematic block diagram of a retrieval scheme according to a first embodiment based on common mode cancellation.

FIG. 2 shows a schematic block diagram of a retrieval scheme or signal extracting unit according to the first embodiment based on a common mode cancellation (CMC).

Given the above observations, a respiration signal can be retrieved from motion contaminated measurement with the following exemplary multi-step procedure which can be implemented as a software routine for a computer unit or as signal processing scheme for the signal extracting unit.

In a first step or stage (OS) 21, the sensor orientation is estimated. Here, the orientation of the sensors ACC1 and ACC2 is estimated, which is defined as the projection of the gravity onto three axes of a sensor. It may be well estimated by taking the (near) DC components of the accelerometer output, denoted as $$V_{orient}^{(i)} = (d_x^{(i)}, d_y^{(i)}, d_z^{(i)}). \quad (3)$$

The estimation can be realized by low-pass filtering $V_{acc}^{(i)}$ or using more advanced algorithms. Since the typical respiration frequency ranges from 0.1 Hz to 2 Hz, the cutoff of low-pass filtering needs to be below 0.1 Hz.

In a second step or stage (RMC) 22, a rotation matrix is calculated in order to align the two sensors ACC1 and ACC2. The rotation matrix can be computed by solving the equation $$V_{orient}^{(1)} = R^{(2)\to(1)} V_{orient}^{(2)} \quad (4)$$

or $$V_{orient}^{(2)} = R^{(1)\to(2)} V_{orient}^{(1)} \quad (5)$$

where $R^{(2)\to(1)}$ and $R^{(1)\to(2)}$ denote the rotation matrices when rotating the first sensor towards the second and vice versa, respectively. A rotation matrix R is a 3×3 matrix that may be decomposed into multiplications of three sub-rotation matrices $R_x(\theta)$, $R_y(\varphi)$ and $R_z(\psi)$. The three matrices represent, sequentially, a planar rotation of $\theta$ about x-axis, a planar rotation of $\varphi$ about y-axis and a planar rotation of $\psi$ about z-axis. Thus effectively the matrix R contains three unknowns, and Eq. (4) or (5) is solvable.

In a third step or stage (CA) 23, one of the sensors ACC1 and ACC2 is virtually rotated towards the other sensor so that the two coordinate systems of the sensor ACC1 and ACC2 are spatially aligned. If the second sensor turns to the first, the rotation can be realized by multiplying both sides of Eq (2) with $R^{(2)\to(1)}$ $$R^{(2)\to(1)} V_{acc}^{(2)} = R^{(2)\to(1)} V_{resp}^{(2)} + R^{(2)\to(1)} V_{mot}^{(2)} \quad (6)$$

Otherwise, Eq (1) is multiplied by $R^{(1)\to(2)}$.

In a fourth step or stage (MR) 24, motion components are cancelled or removed. Based on the earlier discussed effect in sensing respiration and motion, the following holds:

$$R^{(2)\to(1)} V_{mot}^{(2)} = V_{mot}^{(1)}. \quad (7)$$

Subtracting Eq (6) from Eq (1) using Eq (7) leads to:

$$\tilde{V}_{resp(2)}^{(1)} = V_{acc}^{(1)} - R^{(2)\to(1)} V_{acc}^{(2)} = V_{rep}^{(1)} - R^{(2)\to(1)} V_{resp} \quad (8)$$

where $\tilde{V}_{resp}^{(1)}$ is a newly constructed signal containing respiration components from two original sensor signals that are linearly combined. Similarly, when the first sensor is chosen to rotate, the following equation is obtained:

$$\tilde{V}_{resp(1)}^{(2)} = V_{acc}^{(2)} - R^{(1)\to(2)} V_{acc}^{(1)} = V_{rep}^{(2)} - R^{(1)\to(2)} V_{resp} \quad (9)$$

In both signals, motion induced components have been removed. Further processing can then be carried out on the retrieved respiration signal to extract parameters such as rate and rate variation.

In another implementation of the first embodiment or the other embodiments, for further reducing local and mutual movement, multiple sensors may be connected using materials that are able to limit the moving freedom of the sensors to a certain extent, mainly along the skin surface, but still elastic enough not to restrict breathing and sacrifice wearing comfort.

Figure 3:
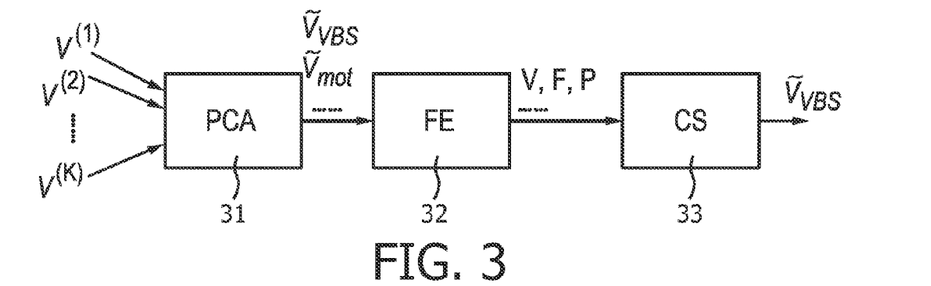
FIG. 3 shows a schematic block diagram of a retrieval scheme according to a second embodiment based on principal component analysis.

FIG. 3 shows a schematic block diagram of a multi-sensor based retrieval scheme according to a second embodiment based on principal component analysis (PCA).

For measuring respiration and/or pulse, at least two acceleration sensors are attached to the subject. The sensors may be tri-axial accelerometers and placed at body locations that are optimal for the measured vital body signal type(s) to obtain an angle change induced by the vital body signals, which differs between the at least two sensors. For instance, for respiration monitoring only, sensors are positioned at the lower (about the $6^{th}$ and $7^{th}$) ribs, roughly halfway between the central and lateral position; for both respiration and pulse measurement, one-third way from the sternum on the coastal arch.

In the second embodiment and also the other embodiments, sensors can be attached around desired body locations separately as discrete components, or being integrated forming an array on a patch. The advantage of a sensor array is that it eases the attachment and can contain more sensor elements due to miniaturization. Another advantage may be that some distorting movements are restricted, for instance, unfavorable mutual movement as mentioned in the previous section.

It is supposed that there are K sensors being used. After appropriate filtering according to the frequency band of the signal of interest and pre-processing, the readout of the i-th sensor can be written as $$V^{(i)} = V_{VBS}^{(i)} + V_{mot}^{(i)} + V_n^{(i)}, i=1,\ldots,K \quad (10)$$

where $V_{VBS}^{(i)}$ is the wanted physiological signal, $V_{mot}^{(i)}$ the motion induced signal and $V_n^{(i)}$ the other signal components mostly containing noise. Note that if tri-axial accelerometers are employed and each axis is treated as a measuring unit, the number of sensor outputs is effectively 3K, thus tripled. Statistically, the K (or 3K) sensor outputs are correlated, but their signal components ($V_{VBS}^{(i)}$, $V_{mot}^{(i)}$ and $V_n^{(i)}$) are statistically uncorrelated with one another since they are induced by independent sources.

In a first step or stage (PCA) 31, a PCA procedure is performed that transforms a number of possibly correlated variables into a smaller number of uncorrelated variables called principal components. The first principal component accounts for as much of the variability in the data as possible, and each succeeding component accounts for as much of the remaining variability as possible. After applying PCA on K (or 3K) sensor outputs, the components that contain only the desired vital body signal and only the motion induced signal can be written as follows $$\tilde{V}_{VBS} = \Sigma_i p_i V_{VBS}^{(i)}, \quad (11)$$

$$\tilde{V}_{mot} = \Sigma_i q_i V_{mot}^{(i)} \quad (12)$$

respectively, where $p_i$ and $q_i$ are PCA coefficients. In this manner, the vital body signal is retrieved from the motion contaminated measurement.

As the signal magnitude caused by motion is usually (much) larger than that of a vital body signal, usually the second principal component is the vital body signal whenever motion is detected. However, for a more reliable result, an advanced component selection method is required, which can be fulfilled with a classification algorithm.

In a second step or stage (FE) 32 of FIG. 3, the procedure or algorithm is adapted to extract parameters (or features) from the resulting components of PCA. Possible features are signal variance, fundamental frequency, periodicity, etc.

In a third step or stage (CS) 33, component selection is achieved by deciding on which one is most likely to be the vital body signal.

Figure 4:
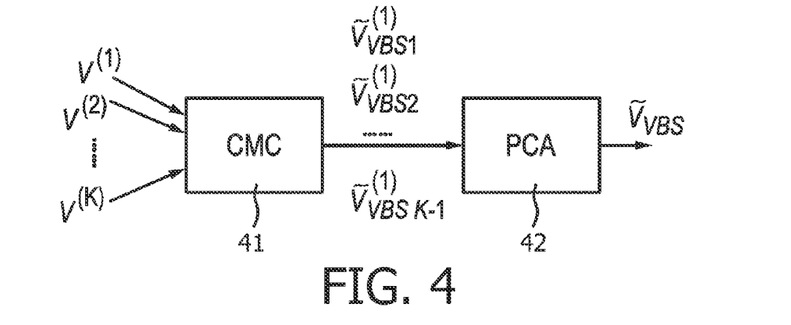
FIG. 4 shows a schematic block diagram of a retrieval approach according to a third embodiment based on cascading common mode cancellation and principal component analysis.

FIG. 4 shows a schematic block diagram of a retrieval approach according to a third embodiment based on cascading CMC and PCA.

Combination of the CMC and PCA methods can be considered, especially when more than two sensors are employed. It is supposed that there are K sensors used.

In a first step or stage (CMC) 41, one of the K sensors is first selected as reference. Then, following the steps or stages in the above CMC retrieval approach, the others are virtually rotated towards the reference sensor to remove the motion components. As a result, K−1 signals are generated. Finally, in a second step or stage (PCA) 42, the above PCA-based retrieval approach is applied on these K−1 signals, to obtain the wanted vital body signal. By cascading the two approaches, the imperfect removal of motion in the CMC can be further tackled, leading to an improved retrieval quality. In the example of FIG. 4, sensor $V^{(i)}$ is selected as the reference sensor.

In the following, a fourth embodiment is described, in which a differential angle measurement (DAM) is applied to retrieve the desired vital body signal.

Sensors such as accelerometers have anisotropic sensitivities. That is, the sensor's output is not independent of the spatial direction of its input. Whenever two or more of such sensors are employed in a way that their inputs are very similar (ideally identical) in some general coordinate system, this anisotropy may be employed to estimate the relative orientations of the local coordinate systems of the different sensors. So, if such sensors can be applied in a way that (changes in) their relative orientations mostly contain information on certain vital body signs, then these vital body signs can be observed in the presence of any non-zero input to the sensors. Whether or not this approach is feasible depends on the general dissimilarity between the inputs at the sensor locations, relative to the magnitude of the orientation change(s) of interest.

As an example, two bi-axial accelerometers can be attached to the skin at two different locations to observe breathing motion. The accelerometers are aligned in such a way, that their measurement axes are (almost) in the same spatial plane. The locations are chosen such that accelerometric inputs are substantially similar in a general coordinate system. In practice, this often means that the distance between the locations has to be small. At the same time, the locations are chosen such that particularly breathing motion results in changes in the relative orientations of the accelerometers.

Figure 5:
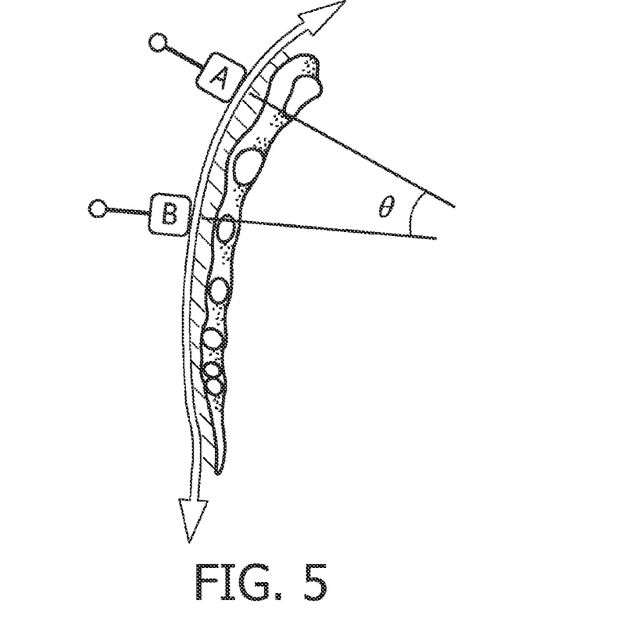
FIG. 5 shows an example of a sensor placement for differential angle measurement according to a fourth embodiment.

FIG. 5 shows an example of a sensor placement, where two accelerometers A, B are placed on top of the sternum. During breathing, the angle θ changes in response to expansion and compression of the thoracic cavity, resulting in measurement of breathing motion. To maximize this effect, two sensors are preferably across the point that separates the main body of the sternum and its upper part, the manubrium. Thereby, orientations between accelerometers are changed, since inhaling stretches the skin over the arched shape of the sternum, thus increasing angle θ, while exhaling reverses the change.

Now, any non-zero accelerometric input that is not purely orthogonal to the direction of the orientation changes suffices to observe the breathing motion. The accelerometric input can be resulting from gravity, e.g., when the measured subject is at rest, or inertial accelerations induced by body movement during activities. Because of its measurement principle, this DAM-based approach is therefore intrinsically robust against motions.

Conventional DAM-based systems can be compared to CMC techniques where two sensors measure the signal differently and the vital body signal is obtained by subtraction. However, in the proposed DAM-based approach according to the fourth embodiment, an angle difference between the acceleration vectors of the two sensors A, B is measured. It is thus not a difference in angles (rotation and/or translation) between the two sensors A, B, but a difference in measured acceleration vectors inside the sensor's systems. The proposed approach is therefore much more insensitive to motion artifacts. The sensors A, B in this case can be positioned on the sternum, e.g., very close together.

Based on this example, the signal related to breathing motion can be derived from the outputs of the accelerometers in the following way, assuming the sensor plane of the two accelerometers is orthogonal to the body surface, $$\theta_A(t) = \tan^{-1} \frac{y_A(t)}{x_A(t)} \quad (13)$$

$$\theta_B(t) = \tan^{-1} \frac{y_B(t)}{x_B(t)} \quad (14)$$

$$\Delta\theta_{AB}(t) = \theta_B(t) - \theta_A(t) \quad (15)$$

where $x_A$, $y_A$, $x_B$, $y_B$ are the output signals of the x- and y-axes of accelerometers A and B and $\Delta\theta_{AB}$ is the signal related to breathing motion. Alternatives to this particular method of calculating orientational difference are possible.

It is noted that, following the above mentioned principle, more general procedures can be easily devised for tri-axial accelerometers.

Similarly to the cascaded method of CMC and PCA, if more than one angle is obtained through differential angle measurement, PCA may subsequently be applied in the fourth embodiment to extract components most strongly related to the vital body signal of interest.

Figure 6:
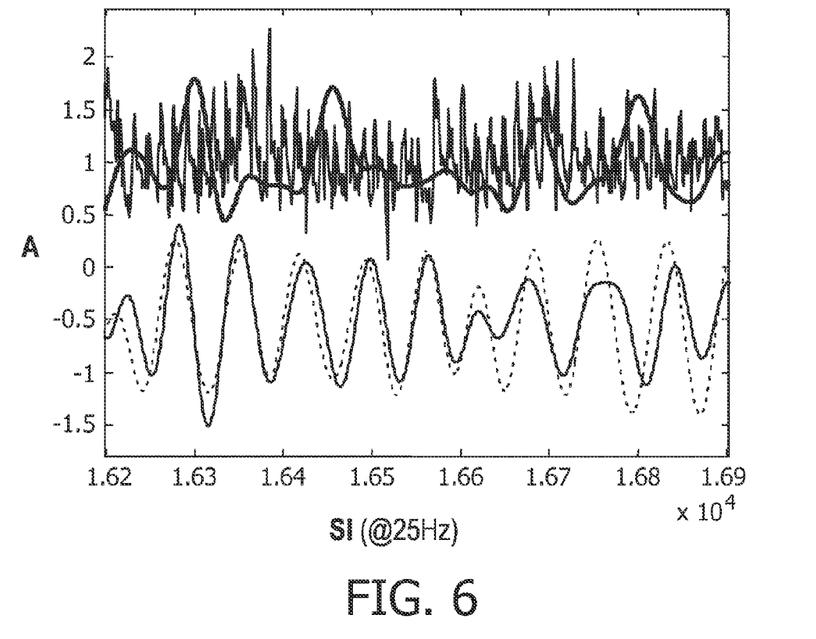
FIG. 6 shows a diagram with measured acceleration and retrieved breathing signals retrieved using principal component analysis.

FIG. 6 shows a diagram with measured amplitudes A of acceleration and breathing signals SI retrieved using principal component analysis according to the above second embodiment.

In this example, to measure respiration, three tri-axial accelerometers were placed at the left, right costal arches and abdomen of a test subject. A respiration band around the chest was used as reference. During measurement, the subject performed walking, jogging, lying, sitting and desk work in a lab space under the instruction. The sensor readouts were re-sampled at 25 Hz before further processing. The upper strongly varying waveform of FIG. 6 corresponds to a raw signal measured by x-axis of the left-chest sensor. The upper bold waveform corresponds to its low-pass filtered version (cutoff at 1 Hz). The lower dashed waveform corresponds to the retrieved breathing component, while the lower continuous waveform corresponds to a reference signal of the respiration band.

Considering the readout from each axis as a separate measurement, there were in total 3×3=9 inputs to the PCA method. In FIG. 6, a piece of signal waveform measured during walking is shown, as well as the selected component after PCA that resembles very well the reference breathing signal measured by the respiration band.

Figure 7A:
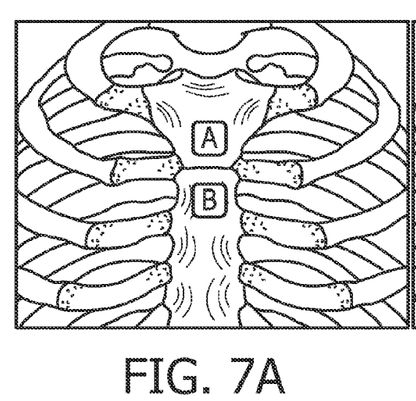
FIGS. 7A-B show examples of placements of accelerometers.
Figure 7B:
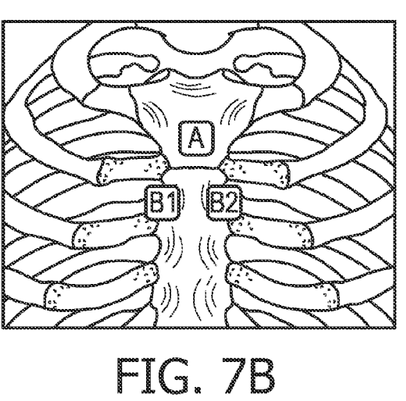

In another experiment, accelerometers A, B and A, B1, B2, respectively, were placed as illustrated in FIGS. 7A and 7B with respect to bony structures. The left FIG. 7A shows the basic configuration with two accelerometers A, B and the right FIG. 7B shows an improved version with three accelerometers A, B1, and B2 that was adopted in the experiment. With the improved configuration, signals from the accelerometers B1 and B2 are averaged to form a more stable alternative to that from the single accelerometer B.

Figure 8:
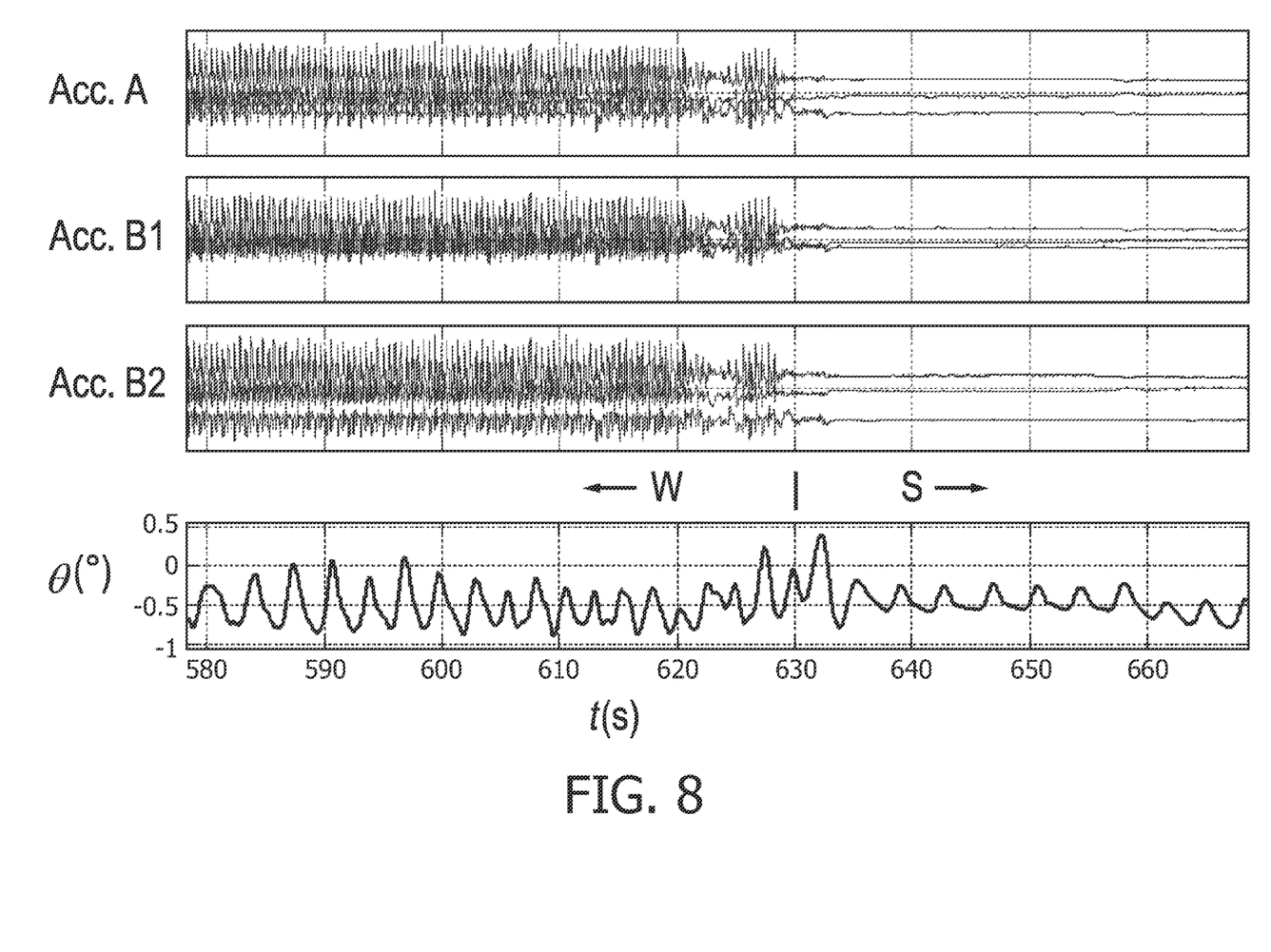
FIG. 8 shows a diagram with measured acceleration signals and retrieved breathing signals during walking and sitting using differential angle measurement.

FIG. 8 shows accelerations waveforms measured by the accelerometers A, B1 and B2 of FIG. 7B during walking W and sitting S in the upper three rows, and a retrieved breathing signal using the DAM method in the last row.

In the first three rows of FIG. 8, different waveforms represent readouts from different accelerometer axes. The last row shows the angle θ calculated according to the above DAM formula and subsequently low pass filtered with a cut-off frequency of 1 Hz.

This invention can be applied in all settings where vital body signs, such as respiration, are monitored using body-worn sensors, e.g., accelerometers. Targeted applications range from patient monitoring in hospitals, through healthcare at homes or nursing centers, and to consumer lifestyle applications, such as vital body sign measurement during fitness and sport.

In summary, a multi-sensor system and method of monitoring vital body signals during movement of a body of a human or an animal has been described, wherein acceleration sensors are placed at body locations in such a way that an acceleration angle change induced by said vital body signals differs between said at least two acceleration sensors. The retrieval of the vital body signals is achieved by extracting a wanted vital body signal based on measurement results from multiple sensors that may be motion contaminated. Three retrieval schemes are proposed, each with preferred sensor locations that provide optimal performance of retrieving the vital body signal(s).

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor, sensing unit or other unit may fulfill the functions of several items recited in the claims. The mere fact that certain measures are recited in mutually different dependent claims does not indicate that a combination of these measures cannot be used to advantage.

It is noted that the proposed solution according to the above embodiments can be implemented at least partially in software modules at the relevant functional blocks of FIGS. 2 to 4. The resulting computer program product may comprise code means for causing a computer to carry out the steps of the above procedures of functions of FIGS. 2 to 4. Hence, the procedural steps are produced by the computer program product when run on the computer. The computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope thereof.

The present invention relates to a multi-sensor system and method of monitoring vital body signals during movement of a body of a human or an animal, wherein acceleration sensors are placed at body locations in such a way that an acceleration angle change induced by said vital body signals differs between said at least two acceleration sensors. The retrieval of the vital body signals is achieved by extracting a wanted vital body signal based on measurement results from multiple sensors that may be motion contaminated. Three retrieval schemes are proposed, each with preferred sensor locations that provide optimal performance of retrieving the vital body signal(s).

The invention claimed is:

1. A method of monitoring respiration signals on a body of a human or animal, the method comprising:
   placing at least two tri-axial acceleration sensors on a sternum of said body with the at least two acceleration sensors separated by the point that separates the main body of the sternum and a manubrium in such a way that an angle change induced by said respiration signals differs between said at least two acceleration sensors,
   using said at least two acceleration sensors to measure respective acceleration vectors; and
   retrieving said respiration signals by applying differential angle measurement to the acceleration vectors measured by said at least two acceleration sensors to extract said respiration signals.

2. The method according to claim 1, wherein said retrieving comprises applying said differential angle measurement by measuring an angle difference between acceleration vectors of said at least two acceleration sensors.

3. The method according to claim 2, wherein said placing comprises aligning said at least two acceleration sensors in such a way that their measurement axes are substantially in the same spatial plane.

4. The method according to claim 1, further comprising using said at least two acceleration sensors in respiration sensing as inclinometers to reflect chest movement caused by respiration.

5. The method according to claim 1, further comprising using said at least two acceleration sensors in pulse sensing to catch mechanical vibration caused by heart pumping.

6. A method of monitoring respiration signals on a body of a human, the method comprising:
   placing two tri-axial acceleration sensors on top of a sternum of said body with the two acceleration sensors separated by the point that separates the main body of the sternum and a manubrium;

using said two acceleration sensors to measure respective acceleration vectors; and retrieving said respiration signals by applying differential angle measurement to the acceleration vectors measured by said two acceleration sensors to extract said respiration signals.

7. The method according to claim 6, wherein said retrieving comprises applying said differential angle measurement by measuring an angle difference between acceleration vectors of said two acceleration sensors.

8. The method according to claim 6, further comprising using said two acceleration sensors in respiration sensing as inclinometers to reflect chest movement caused by respiration.

9. A multi-sensor device for monitoring vital body respiration signals on a body of a human or animal, the device comprising:

at least two acceleration sensors each adapted to measure an acceleration vector and adapted to be placed at predetermined locations on a sternum of said body with the at least two acceleration sensors separated by the point that separates the main body of the sternum and a manubrium in such a way that an angle change induced by said vital body respiration signals differs between said at least two acceleration sensors; and a signal extractor comprising a computer programmed to extract said vital body respiration signals by applying differential angle measurement to measurement results of said at least two acceleration sensors placed at the predetermined locations.

10. The multi-sensor device according to claim 9, wherein said at least two acceleration sensors are tri-axial accelerometers.

11. A signal extracting apparatus for use in the multi-sensor device according to claim 9, said signal extracting apparatus being adapted to extract said vital body respiration signals by applying differential angle measurement to measurement results of said at least two acceleration sensors.

12. The device according to claim 9, wherein the at least two acceleration sensors are configured, in respiration sensing, as inclinometers to reflect abdomen or chest movement caused by respiration or in pulse sensing to catch mechanical vibration caused by heart pumping.

* * * * *